United States Patent [19]

Yamaguchi et al.

[11] Patent Number: 4,804,672

[45] Date of Patent: Feb. 14, 1989

[54] 2-OXO-IMIDAZOLIDINE DERIVATIVES AS AGENTS FOR TREATMENT OF KIDNEY DISEASES

[75] Inventors: Isao Yamaguchi, Tokyo; Shinsuke Nishiyama, Omiya; Masami Kubo, Osaka, all of Japan

[73] Assignee: Tanabe Seiyaku Co., Ltd., Osaka, Japan

[21] Appl. No.: 131,355

[22] Filed: Dec. 10, 1987

[30] Foreign Application Priority Data

Dec. 12, 1986 [JP] Japan .................................. 61-297113

[51] Int. Cl.$^4$ ........................................... A61K 31/415
[52] U.S. Cl. ..................... 514/392; 548/321
[58] Field of Search ......................................... 514/352

[56] References Cited

PUBLICATIONS

*Chemical Abstracts*, 100:174,827y (1984) [EP 95,163, Yoneda et al., 11/30/83].
*Chemical Abstracts*, 103:116,288z (1985) [Japan Kokai, 60 13,715, 1/24/85].
McCaa, R., in *Frontiers in Hypertension Research*, Laragh, J. et al., (editors), Springer-Verlag, New York, 1981, pp. 139–140.

*Primary Examiner*—Richard A. Schwartz
*Attorney, Agent, or Firm*—Birch, Stewart, Kolasch & Birch

[57] ABSTRACT

Novel agent for the treatment of kidney diseases, which comprises as an active ingredient a 2-oxo-imidazolidine compound of the formula:

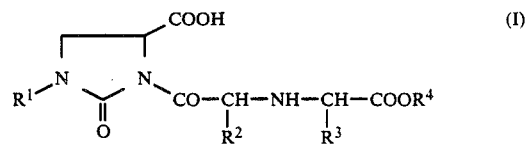

wherein $R^1$ is a lower alkyl group, $R^2$ is a lower alkyl group, $R^3$ is a phenyl-substituted lower alkyl group, and $R^4$ is hydrogen atom or a lower alkyl group, or a pharmaceutically acceptable salt thereof.

7 Claims, No Drawings

2-OXO-IMIDAZOLIDINE DERIVATIVES AS AGENTS FOR TREATMENT OF KIDNEY DISEASES

This invention relates to a novel agent for the treatment of kidney diseases, more particularly, to an agent for the treatment of kidney diseases which comprises as an active ingredient a 2-oxo-imidazolidine compound of the formula:

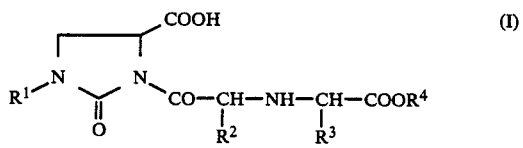

wherein $R^1$ is a lower alkyl group, $R^2$ is a lower alkyl group, $R^3$ is a phenyl-substituted lower alkyl group, and $R^4$ is hydrogen atom or a lower alkyl group, or a pharmaceutically acceptable salt thereof.

TECHNICAL BACKGROUND

It is known that the kidney is an important organ which has a function of maintaining the composition of body fluids normally by controlling excretion of water and salts in the body fluids, and that when the renal function is disturbed, it results in a decrease in renal blood flow and thereby a decrease in excretion of salts, particularly sodium (cf. "Rinsho Yakurigaku Taikei" (Test for Clinical Pharmacology), Vol. 8, Diuretics Transfusion, pages 54–55, issued by Yamanaka Shoten, 1966).

In order to remedy the kidney deseases, it is useful to use a medicament having increasing effects on the renal blood flow and also on the excretion of sodium.

OBJECT OF THE INVENTION

The present inventors have intensively studied to obtain a new agent for the treatment of the kidney diseases, and have found that some imidazolidine compounds are effective for increasing renal blood flow and also increasing excretion of sodium and thereby are useful as an agent for the treatment of kidney diseases.

An object of the invention is to provide a novel medicament for the treatment of kidney diseases. Another object of the invention is to provide an agent for the treatment of kidney diseases according to increasing effects on renal blood flow and on excretion of sodium. These and other objects and advantages of the invention will be apparent to those skilled in the art from the following description.

DETAILED DESCRIPTION OF THE INVENTION

The agent for the treatment of kidney diseases of this invention comprises as an active ingredient a 2-oxo-imidazolidine compound of the formula (I) or a pharmaceutically acceptable salt thereof.

The active compound includes the compounds of the formula (I) wherein $R^1$ is an alkyl group having 1 to 4 carbon atoms, such as methyl, ethyl, n-propyl, isopropyl, n-butyl, isobutyl, etc.; $R^2$ is an alkyl group having 1 to 4 carbon atoms, such as methyl, ethyl, n-propyl, isopropyl, n-butyl, isobutyl, etc.; $R^3$ is a phenyl-substituted alkyl group having 1 to 4 carbon atoms in the alkyl moiety, such as benzyl, phenethyl, phenylpropyl, phenylbutyl, etc.; and $R^4$ is hydrogen atom, or an alkyl group having 1 to 4 carbon atoms, such as methyl, ethyl, n-propyl, isopropyl, n-butyl, isobutyl, etc.

Preferred compounds are the compounds of the formula (I) wherein $R^1$ is methyl, $R^2$ is methyl, $R^3$ is phenethyl, and $R^4$ is hydrogen atom or ethyl.

The compounds (I) of this invention contain three asymmetric carbons within the molecule and hence include four diastereoisomers and eight optical isomers. This invention includes these isomers. Among these isomers, however, the compounds particularly suitable for the intended medical use are the compounds of the formula (I) wherein the carbon atoms at 4-position of the oxoimidazolidine ring and at 2-position of the amino acid moiety of the formula: $-NH-CH(R^3)COOR^4$ are both S-configuration. Other compounds suitable for the medical use are the compounds of the formula (I) wherein the carbon atoms at 4-position of the oxoimidazolidine ring, at 2-position of the alkanoyl moiety of the formula: $-COCH(R^2)-$ and at 2-position of the amino acid moiety of the formula: $-NH-CH(R^3)COOR^4$ are all S-configuration.

The 2-oxo-imidazolidine compounds (I) or a pharmaceutically acceptable salt thereof have increasing effects on renal blood flow and on excretion of sodium.

For instance, when (4S)-1-methyl-3-[(2S)-2-[N-((1S)-1-carboxy-3-phenylpropyl)amino]propionyl]-2-oxoimidazolidine-4-carboxylic acid was intraveneously administered to Beagles under anesthesia at a dose of 10 μg/kg, the compound showed remarkable increasing effects on renal blood flow and on excretion of sodium and further on Na/K ratio without substantial increase in excretion of potassium. Likewise, when (4S)-1-methyl-3-[(2S)-2-[N-((1S)-1-ethoxycarbonyl-3-phenylpropyl)amino]propionyl]-2-oxoimidazolidine-4-carboxylic acid was adminstered into the duodenal tract of the animal at a dose of 10 mg/kg, similar effect was obtained, and the effect was characteristically durable for a long period of time.

Moreover, the compounds (I) of this invention have low toxicity. For instance, when (4S)-1-methyl-3-[(2S)-2-[N-((1S)-1-carboxy-3-phenylpropyl)amino]propionyl]-2-oxoimidazolidine-4-carboxylic acid or (4S)-1-methyl-3-[(2S)-2-[N-((1S)-1-ethoxycarbonyl-3-phenylpropyl)amino]propionyl]-2-oxo-imidazolidine-4-carboxylic acid was orally administered to rats at a dose of 5 g/kg, even after observing for 5 days, no rat was died.

The compounds (I) used as an active ingredient in this invention may be used in any form of a free acid (and/or free base) or a pharmaceutically acceptable salt thereof. The free acid (or base) can be converted into its salt by treating it with an organic or inorganic acid or alternatively with an organic or inorganic base in a usual manner. The pharmaceutically acceptable salts of the compounds (I) include organic acid addition salts (e.g. succinate, meleate, fumarate, methanesulfonate, etc.), inorganic acid addition salts (e.g. hydrochloride, hydrobromide, sulfate, phosphate, etc.), salts with organic bases e.g. lysine salt, ornithine salt, etc.), and salts with inorganic bases (e.g. sodium salt, potassium salt, calcium salt, magnesium salt, etc.).

The compounds (I) or their pharmaceutically acceptable salts thereof have excellent increasing effects on renal blood flow and on excretion of sodium and hence are useful for the treatment of various kidney diseases, such as edema, acute renal failure, progressive renal failure, productive nephritis, and the like in a warm-blooded animal including human being.

The agent of the invention containing as an active ingredient the compound (I) or a pharmaceutically acceptable salt thereof can be administered by the oral route or by the parenteral route. The dose of the compound (I) or a pharmaceutically acceptable salt thereof may vary depending on the severity of diseases, age, weight and body conditions of the patients and the like, but is usually in the range of 0.1 to 100 mg/kg/day, preferably 0.5 to 50 mg/kg/day, in case of oral administration, and in the range of 0.001 to 10 mg/kg/day, preferably 0.005 to 5 mg/kg/day, in case of parenteral adminstration.

The compounds (I) of their pharmaceutically acceptable salts may be used in the form of conventional pharmaceutical preparations in admixture with conventional pharmaceutically acceptable carrier or diluent which are usually used for the pharmaceutical preparations suitable for oral or parenteral administration. The pharmaceutically acceptable carrier or diluent includes, for example, starch, lactose, glucose, potassium phosphate, corn starch, gum arabic, magnesium stearate, and the like. The pharmaceutical preparations include solid preparations such as tablets, pills, capsules, suppositories, and the like, and liquid preparations such as solutions, suspensions, emulsions, and the like. These preparations may be sterilized and may optionally contain other additives, such as stabilizers, wetting agents, emulsifiers, and the like.

The compounds (I) can be prepared by the method as disclosed in European Patent Publication No. 95163 (A2).

The pharmacological activities of the compounds of this invention are illustrated by the following experiments.

EXPERIMENT 1

Male Beagles (weighing 8–10.5 kg, 5 dogs per group) fasted for 18 hours were anesthetized with sodium pentobarbital (30 mg/kg, i.v.) and the anesthetized state was maintained by administering continuously the above medicine (4.5 mg/kg/hr, i.v.).

The test compound: (4S)-1-methyl-3-[(2S)-2-[N-((1S)-1-carboxy-3-phenylpropyl)amino]propionyl]-2-oxo-imidazolidine-4-carboxylic acid sodium salt was intravenously administered to the animals at a dose of 10 µg/kg, and 10 minutes after the administration of test compound, the renal blood flow was measured. Besides, during 20 minutes after the administration of test compound, the urine was collected and the concentration of sodium and potassium in the urine were measured, and the excretion amount of electrolytes and the ratio of Na/K were calculated. The renal blood flow was measured with an electromagnetic flowmeter, the probe of which was placed around the left kidney artery.

The results are shown in Table 1.

TABLE 1

|  | Before administ. of test compound | After administ. of test compound |
| --- | --- | --- |
| Renal blood flow (ml/minute) | 90 ± 12 | 110 ± 12** |
| Na excretion (µEq/minute) | 16 ± 7 | 44 ± 20** |
| K excretion (µEq/minute) | 10 ± 1 | 18 ± 8** |
| Na/K ratio | 1.69 ± 0.70 | 2.69 ± 1.05* |

The mark * means that the data were significant with a level of significance of 5%, and mark ** means that the data were significant with a level of significance of 1%, hereinafter the same.

As is clear from the above experimental results, the active compound of this invention showed excellent increasing effects on renal blood flow and on Na/K ratio.

EXPERIMENT 2

Male Beagles (weighing 8–10.5 kg, 5 dogs per group) anesthetized in the same manner as in Experiment 1 were intraduodenally administered the test compound: (4S)-1-methyl-3-[(2S)-2-[N-((1S)-1-ethoxycarbonyl-3-phenylpropyl)amino]propionyl]-2-oxo-imidazolidine-4-carboxylic acid hydrochloride at a dose of 10 mg/kg, and at an interval of 20 minutes after the administration of test compound, the renal blood flow was measured. Besides, the urine was collected during the above period of time, and the concentrations of sodium and potassium in the urine were measured, and the excretion amount of electrolytes and the ratio of Na/K were calculated. The renal blood flow was measured with an electromagnetic flowmeter, the probe of which was placed around the left kidney artery.

The results are shown in Table 2.

TABLE 2

|  | Before administ. of test compound | After administ. of test compound | | |
| --- | --- | --- | --- | --- |
|  |  | 20 min. | 60 min. | 120 min. |
| Renal blood flow (ml/min.) | 77 ± 2 | 85 ± 8* | 96 ± 8** | 101 ± 9** |
| Na excretion (µEq/min.) | 17 ± 4 | 33 ± 6* | 54 ± 12° | 47 ± 11* |
| K excretion (µEq/min.) | 9 ± 1 | 13 ± 1** | 13 ± 2* | 13 ± 2* |
| Na/K ratio | 1.98 ± 0.41 | 2.59 ± 0.33** | 3.95 ± 0.60** | 3.47 ± 0.52* |

As is clear from the above experimental results, the active compound of this invention showed durable increasing effects on renal blood flow and on sodium excretion and also on Na/K ratio.

The preparations of the present agent are illustrated by the following Examples.

EXAMPLE 1

Tablets:
[Formulation]:

| | |
| --- | --- |
| (Active ingredient) (4S)—1-methyl-3-[(2S)—2-[N—((1S)—1-ethoxycarbonyl-3-phenylpropyl)-amino]propionyl]-2-oxo-imidazolidine-4-carboxylic acid | 10 mg |
| Lactose | 86.8 mg |
| Polyvinylpyrrolidone | 5 mg |
| Corn starch | 37 mg |
| Magnesium stearate | 1.2 mg |
| Totally | 140.0 mg |

[Method]:

To the active ingredient are added lactose and corn starch, and the mixture is well mixed, and thereto is added a solution of polyvinylpyrrolidone in purified water, and the mixture is well kneaded to granulate. The granules thus prepared are dried, and thereto is added magnesium stearate, and the mixture is tabletted in a usual manner to give tablets.

EXAMPLE 2

Tablets:
[Formulation]:

| | |
|---|---|
| (Active ingredient) (4S)—1-methyl-3-[(2S)—2-[N—((1S)—1-carboxy-3-phenylpropyl)-amino]propionyl]-2-oxo-imidazolidine-4-carboxylic acid | 10 mg |
| Lactose | 80 mg |
| Polyvinylpyrrolidone | 3.3 mg |
| Corn starch | 35.9 mg |
| Magnesium stearate | 0.8 mg |
| Totally | 130.0 mg |

[Method]:
In the same manner as described in Example 1, the tablets are prepared.

EXAMPLE 3

Injections:
[Formulation]:

| | |
|---|---|
| (Active ingredient) (4S)—1-methyl-3-[(2S)—2-[N—((1S)—1-ethoxycarbonyl-3-phenylpropyl)-amino]propionyl]-2-oxo-imidazolidine-4-carboxylic acid | 10 mg |
| Sodium chloride | 9 mg |
| Distilled water for injection | q.s. |
| Totally | 1 ml |

[Method]:
The active ingredient and sodium chloride are dissolved in distilled water for injection, and the solution is filtered with a filter (pore size: 0.22 μm), and filled in ampoules and then sterilized to give injections.

EXAMPLE 4

Injections:
[Formulation]:

| | |
|---|---|
| (Active ingredient) (4S)—1-methyl-3-[(2S)—2-[N—((1S)—1-carboxy-3-phenylpropyl)-amino]propionyl]-2-oxo-imidazolidine-4-carboxylic acid | 8.54 mg |
| Sodium chloride | 9.0 mg |
| Sodium hydrogen carbonate | 8.4 mg |
| Distilled water for injection | q.s. |
| Totally | 1 ml |

[Method]:
Sodium chloride is dissolved in distilled water for injection, and thereto is added the active ingredient, and the mixture is dissovled with sodium hydrogen carbonate. The solution is silterd with a filter (pore size: 0.22 μm). The solution is filled in ampoules and then sterilized to give injections.

What is claimed is:

1. A method for the treatment of kidney diseases in a warm-blooded animal, which comprises administering to said warm-blooded animal a therapeutically effective amount of a 2-oxo-imidazolidine compound of the formula:

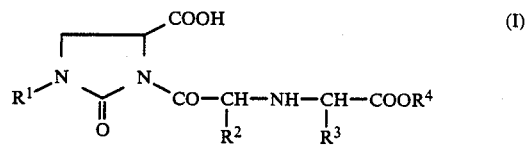

wherein $R^1$ is a lower alkyl group, $R^2$ is a lower alkyl group, $R^3$ is a phenyl-substituted lower alkyl group, and $R^4$ is hydrogen atom or a lower alkyl group, or a pharmaceutically acceptable salt thereof.

2. The method according to claim 1, wherein the compound to be administered is a compound of formula (I) wherein $R^1$ is an alkyl group having 1 to 4 carbon atoms, $R^2$ is an alkyl group having 1 to 4 carbon atoms, $R^3$ is a phenyl-substituted alkyl group having 1 to 4 carbon atoms in the alkyl moiety, and $R^4$ is hydrogen atom, or an alkyl group having 1 to 4 carbon atoms or a pharmaceutically acceptable salt thereof.

3. The method according to claim 1, wherein the compound to be adminstered is a compound of the formula (I) wherein $R^1$ is methyl, $R^2$ is methyl, $R^3$ is phenethyl, and $R^4$ is hydrogen atom or ethyl or a pharmaceutically acceptable salt thereof.

4. The method according to claim 1, wherein the compound to be administered is a compound of the formula (I) wherein the carbon atoms at 4-position of the oxoimidazolidine ring and at 2-position of the amino acid moiety of the formula: $-NH-CH(R^3)COOR^4$ are both S-configuration or a pharmaceutically acceptable salt thereof.

5. The method according to claim 1, wherein the compound to be administered is a compound of the formula (I) wherein the carbon atoms at 4-position of the oxoimidazolidine ring, at 2-position of the alkanoyl moiety of the formula: $-COCH(R^2)-$ and at 2-position of the amino acid moiety of the formula: $-NH-CH(R^3)COOR^4$ are all S-configuration or a pharmaceutically acceptable salt thereof.

6. The method according to claim 1, wherein the compound to be administered is (4S)-1-methyl-3-[(2S)-2-[N-((1S)-1-ethoxycarbonyl-3-phenylpropyl)amino]-propionyl]-2-oxo-imidazolidne-4-carboxylic acid or a pharmaceutically acceptable salt thereof.

7. The method according to claim 1, wherein the compound to be administered is (4S)-1-methyl-3-[(2S)-2-[N-((1S)-1-carboxy-3-phenylpropyl)amino]propionyl]-2-oxo-imidazolidine-4-carboxylic acid or a pharmaceutically acceptable salt thereof.

* * * * *